(12) United States Patent
El-Araby et al.

(10) Patent No.: US 11,648,248 B1
(45) Date of Patent: May 16, 2023

(54) POTENT ANTIMICROBIAL COMPOUNDS WITH A PYRIDAZINE NUCLEUS

(71) Applicant: King Abdulaziz University, Jeddah (SA)

(72) Inventors: Moustafa El-Araby, Jeddah (SA); Khaled Abouzid, Jeddah (SA); Abdelsattar Omar, Jeddah (SA); Maiy Jaballah, Jeddah (SA); Khadijah Mohammad, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/573,777

(22) Filed: Jan. 12, 2022

(51) Int. Cl.
*A61K 31/50* (2006.01)
*A61P 31/04* (2006.01)

(52) U.S. Cl.
CPC .............. *A61K 31/50* (2013.01); *A61P 31/04* (2018.01)

(58) Field of Classification Search
CPC ................................ A61K 31/50; A61P 31/04
See application file for complete search history.

(56) References Cited

U.S. PATENT DOCUMENTS

| | | | |
|---|---|---|---|
| 7,351,834 | B1 | 4/2008 | Riedl |
| 9,029,401 | B2 | 5/2015 | Hammock |
| 2015/0175545 | A1 | 6/2015 | Feng et al. |
| 2018/0029997 | A1 | 2/2018 | Chang et al. |
| 2019/0307751 | A1 | 10/2019 | Allen et al. |
| 2021/0009550 | A1 | 1/2021 | Le et al. |

FOREIGN PATENT DOCUMENTS

WO 2012139499 10/2012

OTHER PUBLICATIONS

Bansal et al., Critical Care 2008, 12(Suppl 5): P38 (Year: 2008).*
Ashok et al, Asian Journal of Chemistry, vol. 28, No. 10 (2016), 2122-2130. (Year: 2016).*

* cited by examiner

*Primary Examiner* — Jean P Cornet
(74) *Attorney, Agent, or Firm* — WCF IP

(57) ABSTRACT

Anti-microbial compounds having a pyridazine nucleus are provided. The compounds have anti-microbial (anti-biotic) properties and are used to treat infections caused by microbes, especially bacteria that are resistant to known antibiotics e.g. drug resistant bacteria such as methicillin-resistant *Staphylococcus aureus* (MRSA).

7 Claims, 3 Drawing Sheets

POTENT ANTIMICROBIAL COMPOUNDS WITH A PYRIDAZINE NUCLEUS

BACKGROUND OF THE INVENTION

Field of the Invention

The invention generally relates to anti-microbial compounds. In particular, the invention provides new, potent anti-microbial compounds having a pyridazine nucleus, and uses thereof to treat infections caused by microbes, especially bacteria that are resistant to known antibiotics.

Description of Related Art

Infectious diseases, especially those caused by multidrug-resistant (MDR) organisms, have become a worldwide health emergency. Methicillin-resistant *Staphylococcus aureus* (MRSA) is a main drug-resistant bacteria and for its property to resist most types of antibiotics, it is considered the most threatening to human health.[1,2,3]

Persistence phenomena is an additional challenge by which a subpopulation of bacteria switches into persistent cells by reinitiating of the organism after termination of an antibiotic course, thereby becoming tolerant towards current antibiotics.[1,4]

Furthermore, several antibiotics lack the capability to eliminate biofilms, which are slimy extracellular matrices by which bacteria adhere to each other and largely collect in a dormant persister state.[4]

According to the Centers for Disease Control and Prevention (CDC), MRSA is classified as a serious threat with more than 80,461 infections and 11,285 deaths per year in USA alone as stated in the antibiotic resistance threats report in 2013.[5]

Accordingly, development of new antibacterial agents capable of combating MRSA infections is required.[3,6,7] It is a desperate challenge to discover effective antibiotics since the dramatic rise of multidrug-resistant (MDR) strains.[8-10]

Although there have been some recent discoveries based on natural products, the scope for targeting MRSA is still narrow.[11] Most of the marketed antibiotics target cell-wall biosynthesis, DNA synthesis or protein biosynthesis. However, all of them have already been counteracted via several resistance mechanisms.[4]

Due to the intricate cellular processes that control virulence, survival and viability, many bacterial proteins await exploitation as potential antibacterial targets.

US patent application 20210009550 describes "disinfectant" compounds which are effective antimicrobials, e.g. to kill drug-resistant microbes such as MRSA. However, the generic formulas, e.g. Formula I, contain a urea motif and do not contain a pyridazine ring.

US patent application 20190307751 discloses imipridones that selectively modulate Class A G protein-coupled receptors (GPCRs) and are useful for the treatment of e.g. cancers, psychiatric disorders, and bacterial infections such as MRSA. However, the generic formulas do not contain a pyridazine ring.

US patent application 20180029997 teaches pyridazine-containing compounds for use as antibiotics effective against e.g. methicillin-resistant *Staphylococcus aureus* (MRSA). However, a pyridazine ring is not present in the compounds.

US patent application 20150175545 teaches fluoro-substituted deuterated diphenylurea compounds and their use to treat or prevent tumor and related diseases. The treatment of infections and killing of microbes is not mentioned.

Issued U.S. Pat. No. 9,029,401 describes compounds which are sorafenib derivatives. The compounds inhibit soluble epoxide hydrolase and associated disease conditions. The compounds are used to treat e.g. cancer and various lung diseases such as emphysema, chronic bronchitis, etc. The treatment of infections and killing of microbes is not mentioned.

Issued U.S. Pat. No. 7,351,834 discloses ʊ-carboxyaryl substituted diphenyl ureas as raf kinase inhibitors. The compounds are described as useful for treating raf mediated diseases such as solid tumors. The treatment of infections and killing of microbes is not mentioned.

WO2012139499 discloses urea compounds having various degrees of inhibitory activity against a variety of protein kinases. However, the abstract describes only anti-cancer activity, not anti-microbial activity.

El-Halfawy et al. (February 2020) discloses a compound that attenuates MRSA virulence. Jaballah et al. (2019) compounds for use is as antiangiogenic agents, e.g. to treat rheumatoid arthritis, psoriasis, and cancer.

Le et al. (February 2020) describes repurposing human kinase inhibitors (namely sorafenib and derivatives thereof) to create an antibiotic active against drug-resistant *Staphylococcus aureus*. In particular, the most active compound, PK150, is very different.

Sadeghian-Rizi (2018) describes the synthesis and characterization of some novel diaryl urea derivatives bearing quinoxalindione moiety for treating cancer.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Pyridazine scaffolds are considered privileged moieties due to their wide spectrum of activity, chemical stability, and synthetic feasibility. Herein, pyridazine-containing compounds with potent anti-bacterial activity at submicromolar concentrations, even against drug resistant strains of bacteria, are described. Exemplary compounds are depicted in FIG. 2. Accordingly, methods of inhibiting or killing microbes which cause infections, including methicillin-resistant *Staphylococcus aureus* (MRSA), are provided. The methods involve contacting the microbes with one or more of the pyridazine-containing antibiotic compounds disclosed herein. In addition, methods of treating bacterial infections in subjects by administering the compounds are provided.

It is an object of this invention to provide a method of treating a bacterial infection in a subject in need thereof, comprising administering to the subject a therapeutically effective amount of at least one compound of general Formula I Formula I

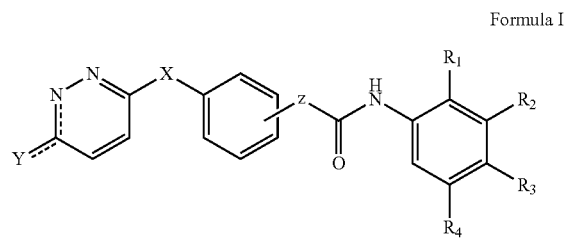

where:
Y=oxygen, Cl or methoxy; X=present or absent and if present is oxygen or NH; Z=3-amino (3-NH) or 4-amino (4-NH) and the attachment between Z and phenyl is ortho, meta or para; R1 is H, methoxy or methyl; R2 is H, methyl, chloro, trifluoromethyl or methoxy; R3 is chloro, methyl or trifluoromethyl; R4 is H, methyl, methoxy, trifluoromethyl, chloro, fluoro or bromo; or a free base or pharmaceutically acceptable salt thereof.

In some aspects, the at least one compound is:

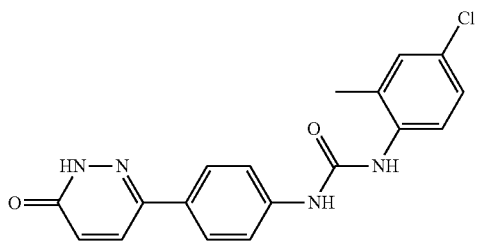

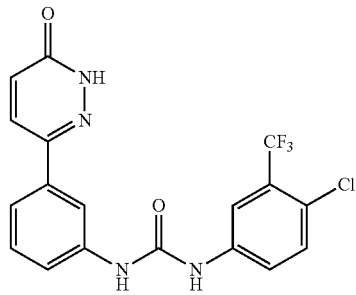

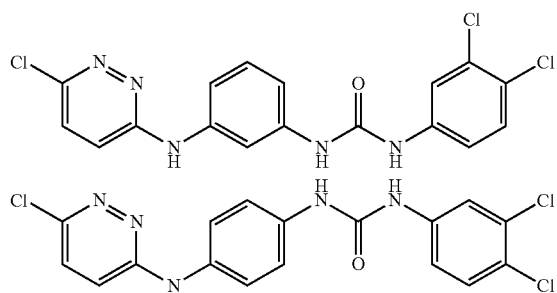

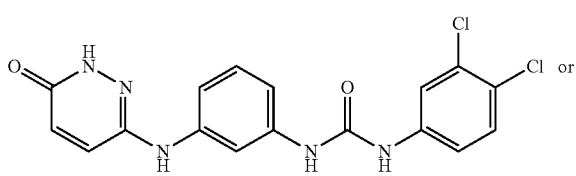

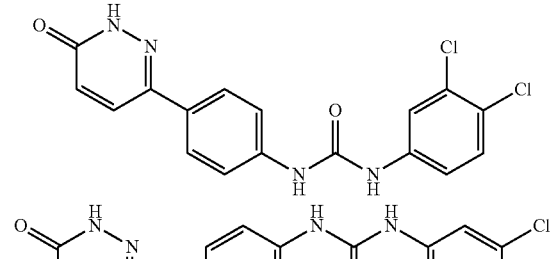

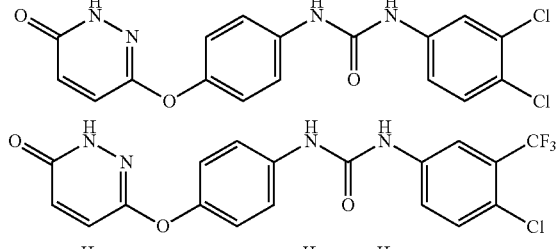

In further aspects, the at least one compound is:

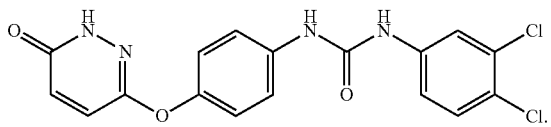 [SMILES: O=C(Nc1ccc(Oc2ccc(=O)[nH]n2)cc1)Nc1ccc(Cl)c(Cl)c1]

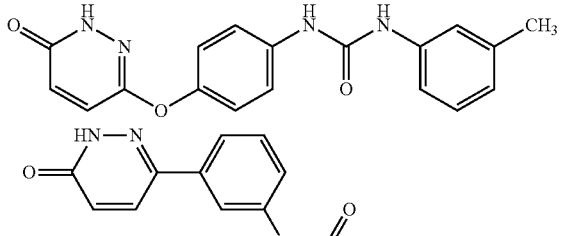

In additional aspects, the bacterial infection is caused by bacteria selected from the group consisting of *Staphylococcus aureus, Staphylococcus epidermidis, Streptococcus pneumoniae, Enterococcus fecalis, Enterococcus faecium* and *Listeria monocytogenes*.

In other aspects, the bacteria are drug resistant bacteria.

In some aspects, the drug resistant bacteria are methicillin-resistant *Staphylococcus aureus* (MRSA).

The invention also provides a method of inhibiting the growth of and/or killing a bacterium, comprising contacting the bacterium with a pyridazine compound of general Formula I Formula I

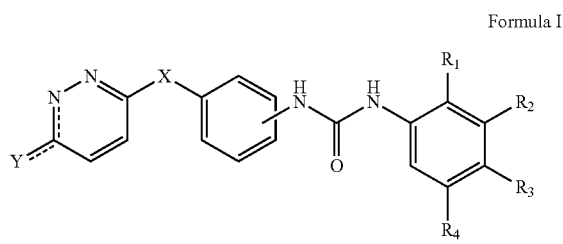

where: Y=oxygen, Cl or methoxy, sulfur; X=present or absent and if present is oxygen or NH; R1 is H, methoxy or methyl; R2 is H, methyl, chloro, trifluoromethyl or methoxy; R3 is chloro, methyl or trifluoromethyl; R4 is H, methyl, methoxy, trifluoromethyl, chloro, fluoro or bromo; and the attachment between the urea moiety and the unsubstituted phenyl is ortho, mew or para; or a free base or pharmaceutically acceptable salt thereof.

In some aspects, the pyridazine compound is:

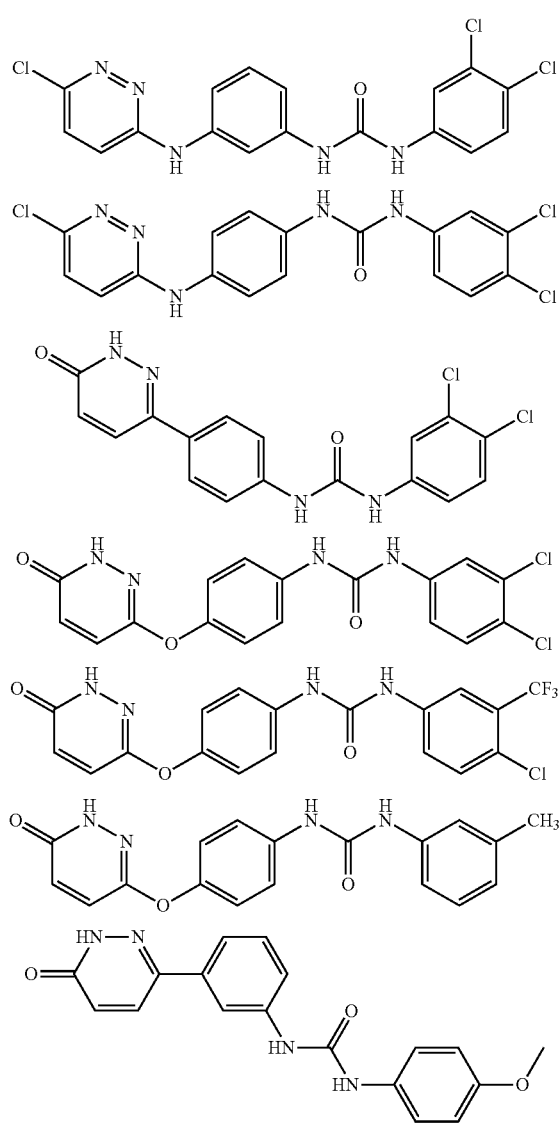

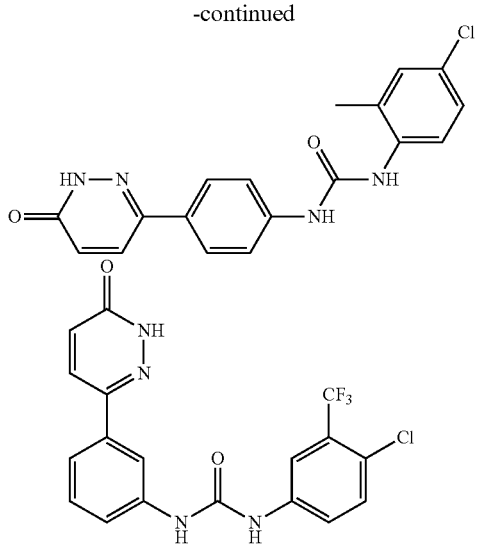

In further aspects, the pyridazine compound is:

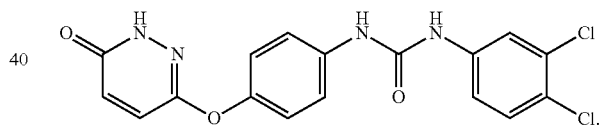

In additional aspects, the pyridazine compound is a pharmaceutically acceptable salt.

In yet further aspects, the pharmaceutically acceptable salt is an organic salt or an inorganic salt.

In some aspects, the organic salt is a, mesylate, tosylate, citrate, acetate, maleate, fumarate, lactate, sulfate salt and the inorganic salt is a hydrochloride or hydrobromide salt.

In other aspects, the bacterium is selected from the group consisting of *Staphylococcus aureus, Staphylococcus epidermidis, Streptococcus pneumoniae, Enterococcus* fecalis, *Enterococcus faecium* and *Listeria monocytogenes*.

In other aspects, the bacterium is a drug resistant bacterium.

In yet further aspects, the drug resistant bacterium is methicillin-resistant *Staphylococcus aureus* (MRSA).

DETAILED DESCRIPTION

Figure 1:
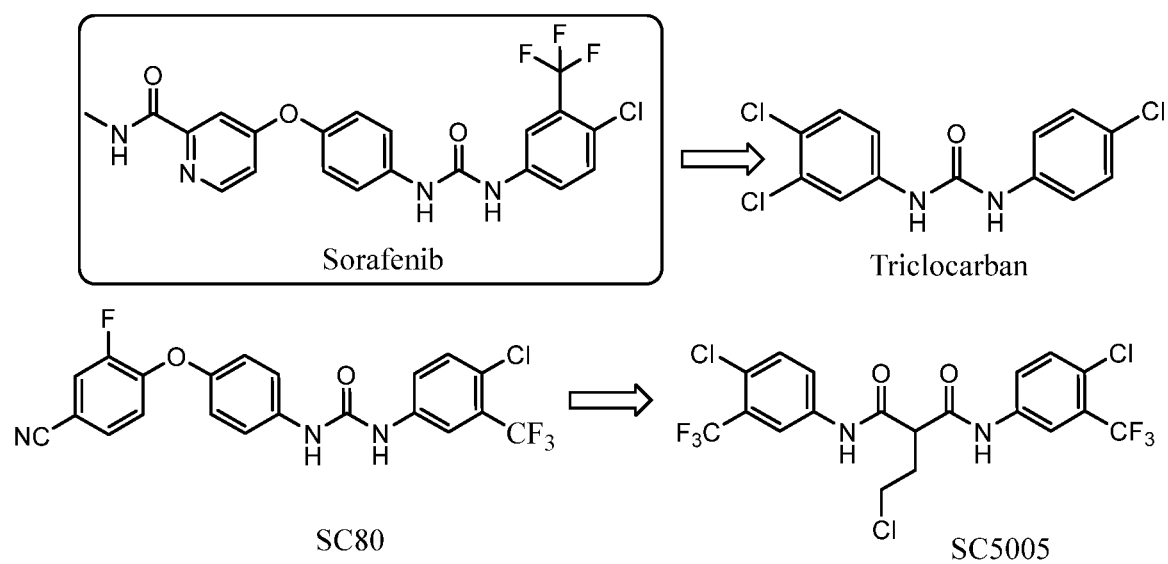
FIG. 1. Structures of prior art pyridazine peptide antibiotics sorafenib and related compounds SC80 and SC5005.

The disclosure provides a new class of compounds with confirmed potency against infectious agents. In particular, the compounds are effective at killing drug resistant bacteria e.g. MRSA and others.

In one aspect, the Formula is as set forth in Formula I:

Formula I

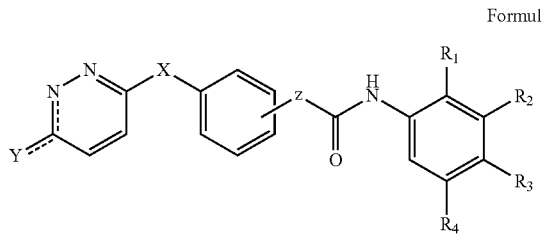

where:
Y=oxygen, Cl or methoxy;
X=present or absent and if present is oxygen or NH;
Z=3-amino (3-NH) or 4-amino (4-NH), and the attachment between Z and phenyl is ortho, mew or para;
R1 is H, methoxy or methyl;
R2 is H, methyl, chloro, trifluoromethyl or methoxy;
R3 is chloro, methyl or trifluoromethyl; and
R4 is H, methyl, methoxy, trifluoromethyl, chloro, fluoro or bromo;
or a free base or pharmaceutically acceptable salt thereof.

In one aspect, the compounds are pyridazine compounds having general Formula II:

Formula II

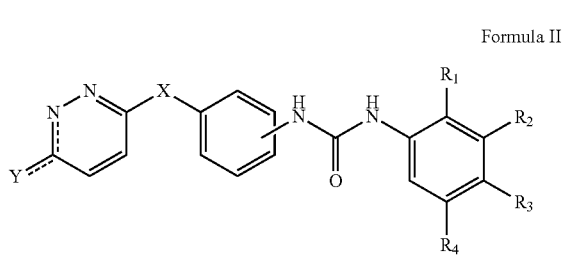

where:
Y=oxygen, Cl, methoxy, or sulfur;
X is present or absent and if present is oxygen or NH;
the attachment between the urea moiety and phenyl is ortho, mew or para;
R1 is H, methoxy or methyl;
R2 is chloro, trifluoromethyl or methoxy;
R3 is H, methyl, chloro, or trifluoromethyl; and
R4 is H, methyl, methoxy, trifluoromethyl, chloro, fluoro or bromo;
or a free base or pharmaceutically acceptable salt thereof.

Exemplary compounds of Formula I include but are not limited to those shown below, which are presented with their informal designations (MY14, MY16, etc.).

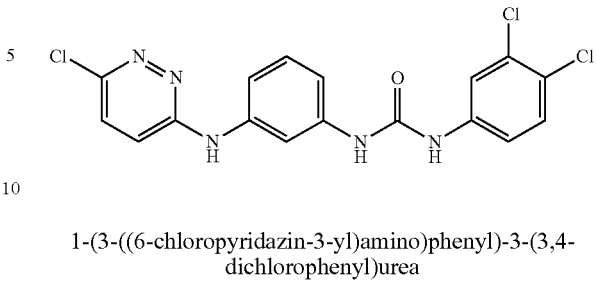

1-(3-((6-chloropyridazin-3-yl)amino)phenyl)-3-(3,4-dichlorophenyl)urea

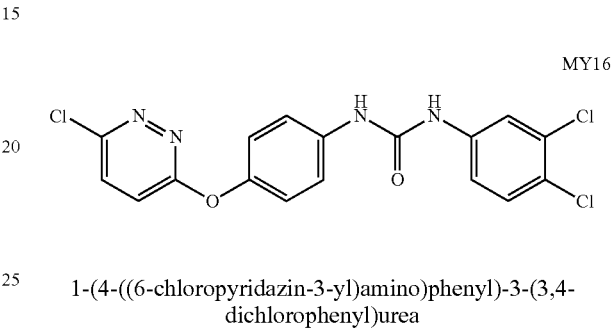

1-(4-((6-chloropyridazin-3-yl)amino)phenyl)-3-(3,4-dichlorophenyl)urea

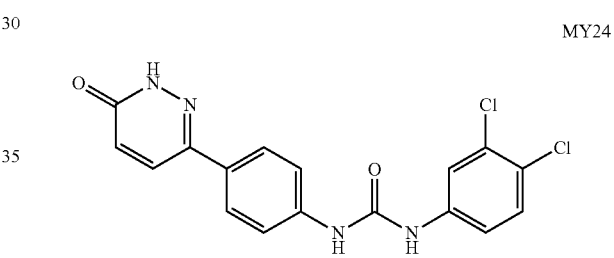

1-(3,4-dichlorophenyl)-3-(4-(6-oxo-1,6-dihydro-pyridazin-3-yl)phenyl)urea

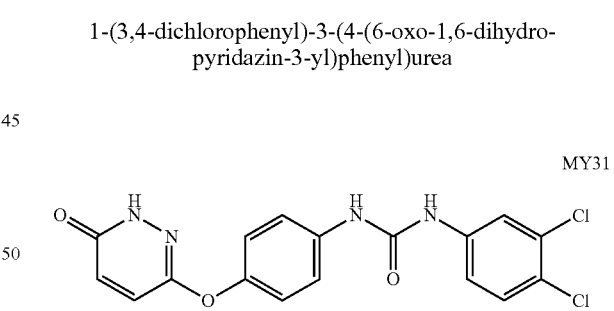

1-(3,4-dichlorophenyl)-3-(4-((6-oxo-1,6-dihydro-pyridazin-3-yl)oxy)phenyl)urea

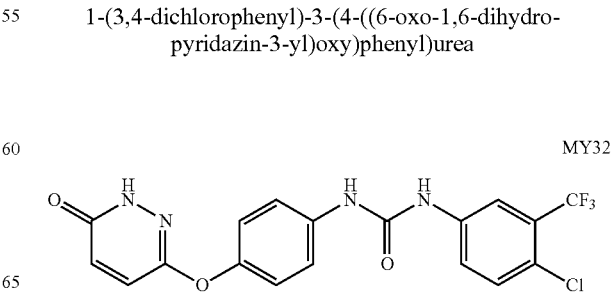

1-(4-chloro-3-(trifluoromethyl)phenyl)-3-(4-((6-oxo-1,6-dihydropyridazin-3-yl)oxy)phenyl)urea 1-(4-chloro-3-(trifluoromethyl)phenyl)-3-(3-(1,6-dihydropyridazin-3-yl)phenyl)urea

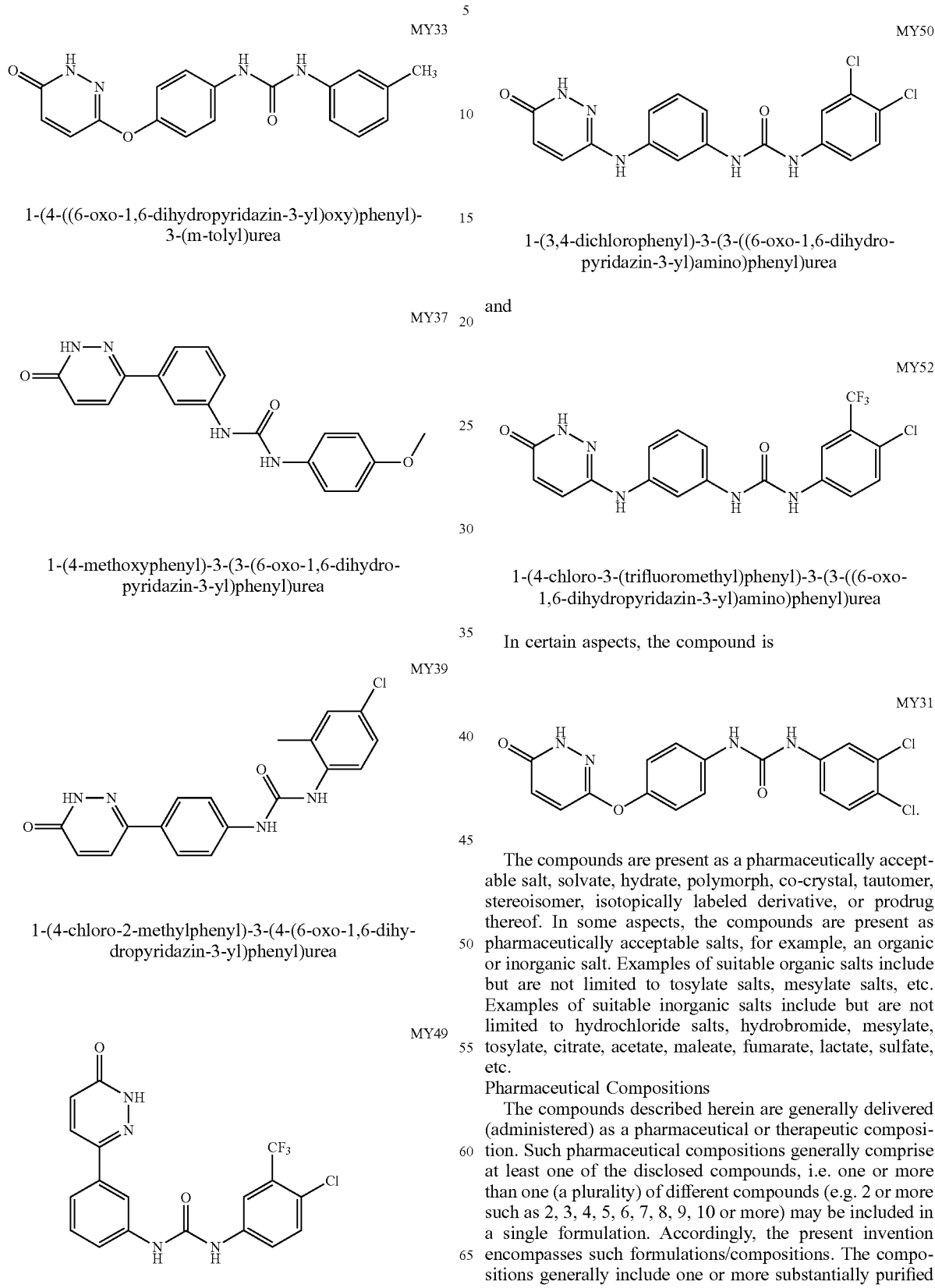

1-(4-((6-oxo-1,6-dihydropyridazin-3-yl)oxy)phenyl)-3-(m-tolyl)urea 1-(3,4-dichlorophenyl)-3-(3-((6-oxo-1,6-dihydropyridazin-3-yl)amino)phenyl)urea and 1-(4-methoxyphenyl)-3-(3-(6-oxo-1,6-dihydropyridazin-3-yl)phenyl)urea 1-(4-chloro-3-(trifluoromethyl)phenyl)-3-(3-((6-oxo-1,6-dihydropyridazin-3-yl)amino)phenyl)urea In certain aspects, the compound is 1-(4-chloro-2-methylphenyl)-3-(4-(6-oxo-1,6-dihydropyridazin-3-yl)phenyl)urea The compounds are present as a pharmaceutically acceptable salt, solvate, hydrate, polymorph, co-crystal, tautomer, stereoisomer, isotopically labeled derivative, or prodrug thereof. In some aspects, the compounds are present as pharmaceutically acceptable salts, for example, an organic or inorganic salt. Examples of suitable organic salts include but are not limited to tosylate salts, mesylate salts, etc. Examples of suitable inorganic salts include but are not limited to hydrochloride salts, hydrobromide, mesylate, tosylate, citrate, acetate, maleate, fumarate, lactate, sulfate, etc.

Pharmaceutical Compositions

The compounds described herein are generally delivered (administered) as a pharmaceutical or therapeutic composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, a composition may contain minor amounts of auxiliary substances such as wetting and/or emulsifying agents, pH buffering agents, preservatives, and the like. In some aspects, it is desired to administer an oral form of the composition so various thickeners, flavorings, diluents, emulsifiers, dispersing aids or binders and the like are added. The compositions of the present invention may contain any such additional ingredients so as to provide the composition in a form suitable for administration. The final amount of compound in the formulations varies but is generally from about 1-99%, and may be, for example, between 0.1% and 100% (w/w) active ingredient. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions. In addition, other non-toxic compatible lubricants such as sodium lauryl sulfate and magnesium stearate, as well as coloring agents, releasing agents, coating agents, sweetening, flavoring and perfuming agents, preservatives and antioxidants may also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are generally preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use, examples of which include but are not limited to ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Administration

The antibiotic compounds are administered in vivo by any suitable route including but not limited to: inoculation or injection (e.g. intravenous, intraperitoneal, intramuscular, subcutaneous, intra-aural, intra-articular, intra-mammary, and the like); topical application (e.g. on areas such as eyes, skin, in ears or on afflictions such as wounds and burns); by absorption through epithelial or mucocutaneous linings (e.g., nasal, oral, vaginal, rectal, gastrointestinal mucosa, and the like); and by inhalation (e.g. as a mist or spray). Formulations suitable for a particular mode of administration are also encompassed, e.g. pills, capsules, liquids, etc. for oral administration; creams, ointments and suppositories for intravaginal or rectal administration; as eye drops for administration to the eye; etc. In some aspects, the compounds are incorporated into dressings or bandages (e.g. lyophilized forms may be included directly in the dressing), etc. to prevent the occurrence of infection in a would or burn. In preferred embodiments, the mode of administration is topical or oral or by injection. In particular, in patients with drug resistant infections, intravenous administration may be preferred.

The compositions may be administered in conjunction with other treatment modalities such as but not limited to: substances that boost the immune system, various chemotherapeutic agents, other antibiotic agents, pain medication, and the like.

Methods

The present invention provides methods of using the compounds disclosed herein. Exemplary methods include but are not limited to: methods of treating a microbial infection, preventing a microbial infection, inhibiting the growth of a microorganism, inhibiting the reproduction of a microorganism, killing a microorganism, inhibiting the formation and/or growth of a biofilm, reducing or removing a biofilm, or disinfecting a surface such as a biological surface (e.g., skin) or a non-biological surface (e.g. medical equipment, counters in medical facilities, etc.) The inventive compounds preferably have minimal or no adverse side effects. In certain embodiments, the inventive compounds have low cytotoxicity with respect to mammalian cells and/or demonstrate low hemolysis activity.

Generally, the methods involve using or administering an effective amount or a prophylactically or therapeutically effective amount of one or more compounds of the invention to a subject in need thereof. The subjects (patients) are generally mammals and may be humans. However, veterinary applications of the compounds e.g. to treat companion pets, livestock, etc. are also encompassed.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. In certain embodiments, an effective amount is an amount effective for inhibiting the growth of a microorganism, for inhibiting the reproduction of a microorganism, or for killing a microorganism. In certain embodiments, an effective amount is an amount effective for inhibiting the formation of a biofilm, for inhibiting the growth of a biofilm, for reducing a biofilm, or for clearing a biofilm. In certain embodiments, an effective amount is an amount effective for disinfecting a surface (e.g., killing at least 80%, at least 90%, at least 99%, at least 99.9%, or at least 99.99% of the microorganisms on the surface). In certain embodiments, an effective amount is an amount effective for killing a persister cell.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. In certain embodiments, a therapeutically effective amount is effective for treating a microbial infection (e.g., a bacterial infection or mycobacterial infection) in a subject, for inhibiting the growth and/or reproduction of a microorganism (e.g., a bacterium), for killing a microorganism (e.g., a bacterium), for inhibiting the formation and/or growth of a biofilm, for reducing or clearing a biofilm, and/or for disinfecting a surface. In some aspects, the therapeutic effect is avoidance or prevention of death of a subject.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a microbial infection (e.g., a bacterial infection or mycobacterial infection) in a subject, for inhibiting the growth and/or reproduction of a microorganism (e.g., a bacterium), for killing a microorganism (e.g., a bacterium), for inhibiting the formation and/or growth of a biofilm, for reducing or clearing a biofilm, and/or for disinfecting a surface.

The exact amount of a compound required to achieve an effective amount will vary from subject to subject, depending, for example, on species, age, and general condition of a subject, severity of the side effects or disorder, identity of the particular compound(s), mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

The compounds or compositions can be administered as the only medicament to treat a subject or in combination with additional pharmaceutical agents, e.g. to improve their potency, efficacy, and/or bioavailability, reduce and/or modify their metabolism, inhibit their excretion, and/or modify their distribution within the body. It will also be appreciated that the therapy employed may achieve a desired effect for the same disorder, and/or it may achieve different effects. In certain embodiments, the combination of a compound of the invention and an additional pharmaceutical agent shows a synergistic effect.

The compound or composition can be administered concurrently with, prior to, or subsequent to, one or more additional pharmaceutical agents, which are different from the compound or composition and may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, other antibiotics (e.g., antibacterial agents, antiviral agents, anti-fungal agents), anti-inflammatory agents, anti-pyretic agents, and pain-relieving agents.

The present compounds may be used to prevent and/or treat any type of infection caused e.g. by bacteria. In some aspects, the bacteria are drug sensitive; in other aspects, the bacteria are resistant to one or more drugs, e.g. one or more antibiotics.

In some aspects, the bacterial infection that is prevented or treated is caused by a bacteria or bacterial strain that is resistant to one or more drugs (antibiotics) that are commonly used to fight microbial infections. In certain embodiments, the microorganism is multidrug-resistant. In certain embodiments, the microorganism is resistant to methicillin, penicillin, ciprofloxacin, rifampin, vancomycin, daptomycin, linezolid, or a combination thereof. In certain embodiments, the microorganism is associated with a biofilm (e.g., present in and/or on a biofilm, able to form a biofilm, and/or able to increase the size of a biofilm). In certain embodiments, the bacterium is a Gram-positive bacterium. In certain embodiments, the bacterium is a multidrug-resistant bacterium. In certain embodiments, the bacterium is a *Staphylococcus* species. In certain embodiments, the bacterium is a *Staphylococcus aureus* (*S. aureus*) strain (e.g., ATCC 25923). In certain embodiments, the bacterium is methicillin-resistant *Staphylococcus aureus* (MRSA). In certain embodiments, the bacterium is the methicillin-resistant *Staphylococcus aureus* clinical isolate (MRSA-2, a clinical isolate from a patient treated at Shands Hospital; obtained from the Emerging Pathogens Institute at the University of Florida), such as the methicillin-resistant *Staphylococcus aureus* clinical isolate reported in Abouelhassan et al., Bioorg. Med. Chem. Lett., 2014, 24, 5076. In certain embodiments, the bacterium is a *Staphylococcus epidermidis* (*S. epidermidis*) strain (e.g., ATCC 12228 or ATCC 35984). In certain embodiments, the bacterium is an MRSE strain. In certain embodiments, the bacterium is a *Staphylococcus auricularis, Staphylococcus carnosus, Staphylococcus condimenti, Staphylococcus massiliensis, Staphylococcus piscifermentans, Staphylococcus simulans, Staphylococcus capitis, Staphylococcus caprae, Staphylococcus saccharolyticus, Staphylococcus devriesei, Staphylococcus haemolyticus, Staphylococcus hominis, Staphylococcus chromogenes, Staphylococcus felis, Staphylococcus delphini, Staphylococcus hyicus, Staphylococcus intermedius, Staphylococcus lutrae, Staphylococcus microti, Staphylococcus muscae, Staphylococcus pseudintermedius, Staphylococcus rostri, Staphylococcus schleiferi, Staphylococcus lugdunensis, Staphylococcus arlettae, Staphylococcus cohnii, Staphylococcus equorum, Staphylococcus gallinarum, Staphylococcus* kloosii, *Staphylococcus* leei, *Staphylococcus nepalensis, Staphylococcus saprophyticus, Staphylococcus succinus, Staphylococcus xylosus, Staphylococcus fleurettii, Staphylococcus lentus, Staphylococcus sciuri, Staphylococcus stepanovicii, Staphylococcus vitulinus, Staphylococcus simulans, Staphylococcus pasteuri*, or *Staphylococcus warneri* strain. In certain embodiments, the bacterium is a *Streptococcus* species. In certain embodiments, the bacterium is a *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus mitis, Streptococcus mutans, Streptococcus oxalis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans*, or *Streptococcus zooepidemicus* strain. In certain embodiments, the bacterium is an *Enterococcus* species. In certain embodiments, the bacterium is an *Enterococcus avium, Enterococcus durans, Enterococcus faecalis, Enterococcus faecium, Enterococcus gallinarum, Enterococcus hirae*, or *Enterococcus solitarius* strain. In certain embodiments, the bacterium is an *Enterococcus faecium* strain (e.g., a vancomycin-resistant strain of *Enterococcus faecium* (VRE); ATCC 700221). In certain embodiments, the bacterium is a *Listeria* species. In certain embodiments, the bacterium is a *Listeria fleischmannii*, *Listeria grayi*, *Listeria innocua*, *Listeria ivanovii*, *Listeria marthii*, *Listeria monocytogenes*, *Listeria rocourtiae*, *Listeria seeligeri*, *Listeria weihenstephanensis*, or *Listeria welshimeri* strain. In certain embodiments, the bacterium is a *Clostridium* species. In certain embodiments, the bacterium is a *Clostridium acetobutylicum*, *Clostridium argentinense*, *Clostridium aerotolerans*, *Clostridium baratii*, *Clostridium beijerinckii*, *Clostridium bifermentans*, *Clostridium botulinum*, *Clostridium butyricum*, *Clostridium cadaveris*, *Clostridium cellulolyticum*, *Clostridium chauvoei*, *Clostridium clostridioforme*, *Clostridium colicanis*, *Clostridium difficile*, *Clostridium estertheticum*, *Clostridium fallax*, *Clostridium feseri*, *Clostridium formicaceticum*, *Clostridium histolyticum*, *Clostridium innocuum*, *Clostridium kluyveri*, *Clostridium ljungdahlii*, *Clostridium lavalense*, *Clostridium leptum*, *Clostridium novyi*, *Clostridium oedematiens*, *Clostridium paraputrificum*, *Clostridium perfringens* (Alias: *Clostridium welchii*), *Clostridium phytofermentans*, *Clostridium piliforme*, *Clostridium ragsdalei*, *Clostridium ramosum*, *Clostridium scatologenes*, *Clostridium septicum*, *Clostridium sordellii*, *Clostridium* sporo genes, *Clostridium sticklandii*, *Clostridium tertium*, *Clostridium tetani*, *Clostridium thermocellum*, *Clostridium thermosaccharolyticum*, or *Clostridium tyrobutyricum* strain.

Examples of the drugs to which the bacteria are or become resistant include but are not limited to one or more of: methicillin, vancomycin, cephalosporin In preferred embodiments, examples of bacteria which cause infections that may be treated as described herein include but are not limited to: *Staphylococcus aureus*, *Staphylococcus epidermidis*, *Streptococcus pneumoniae*, *Enterococcus fecalis*, *Enterococcus faecium* and *Listeria monocytogenes*.

In further embodiments, examples of the drug resistant bacteria include but are not limited to: methicillin-sensitive *Staphylococcus aureus*, vancomycin-resistant *Staphylococcus aureus*, cephalosporin-resistant *Streptococcus pneumoniae*, vancomycin-resistant *Enterococcus fecalis*, vancomycin-resistant *Enterococcus faecium* and *Escherichia coli*.

Specific examples of bacteria and drug resistant bacteria include but are not limited to: *Staphylococcus aureus* ATCC-6538 (MSSA ATCC-6538); Methicillin-sensitive *Staphylococcus aureus* (MSSA NRS-107); Methicillin-resistant *Staphylococcus aureus* (MRSA NRS-119); Methicillin-resistant *Staphylococcus aureus* (MRSA NRS-123, USA400); Vancomycin-resistant *Staphylococcus aureus* (VRSA10); Vancomycin-resistant *Staphylococcus aureus* (VRSA12); *Staphylococcus epidermidis* (NRS-101); Cephalosporin-resistant *Streptococcus pneumoniae* ATCC-15916 (*S. pneumonia* ATCC-15916); Cephalosporin-resistant *Streptococcus pneumoniae* ATCC-700677 (*S. pneumonia* ATCC-700677); Vancomycin-resistant *Enterococcus fecalis* ATCC-51299 (VRE ATCC-51299); Vancomycin-resistant *Enterococcus faecium* ATCC-700221 (VRE ATCC-700221); *Listeria monocytogenes* ATCC-19111 (*L. monocytogenes* ATCC-19111) and *Escherichia coli* JW55031 (TolC mutant); *Escherichia coli* BW25113 (wild-type).

Also encompassed by the invention are kits (e.g., pharmaceutical packs). The kits provided may comprise a compound or composition (e.g., pharmaceutical composition) of the invention and a container (e.g., a vial, ampule, bottle, syringe, dispenser package, tube, inhaler, and/or other suitable container). In some embodiments, a kit of the invention further includes a second container comprising an excipient (e.g., pharmaceutically acceptable excipient) for dilution or suspension of an inventive compound or composition. In some embodiments, the compound or composition of the invention provided in a first container and a second container are combined to form one unit dosage form.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Evaluation of the Antimicrobial Activity of PYRIDAZINE Compounds (MY-Type)

Pyridazines are diazine compounds having two repeated nitrogen atoms.[13] Because the two repeated nitrogens can interact with a targeted protein, drugs containing pyridazine moieties are top selling drugs.[14] The pyridazine architecture is found in drugs with a wide spectrum of biological activity e.g. as antibiotics[13]. Cirratiomycin A and B and Antrimycin are peptide antibiotics having a pyridazine moiety and exhibit antibacterial activity against *Mycobacterium smegmatis* ATCC 607.[15][16]

Non antibiotic drugs are a promising source for the elaboration of novel antibacterial agents.[17] Analogs of sorafenib, which was originally designed as a tyrosine protein kinase inhibitor for cancer therapy, can suppress the growth of *S. aureus* and *Staphylococcus epidermidis*.[12] Sorafenib derivatives SC80 and SC5005 contain N,N'-diaryl urea motifs and exhibit high potency in killing different clinical strains of MRSA with an MIC of 0.5 mg/L and with low cytotoxicity (FIG. 1). Furthermore, SC5005 was selected as a potential lead agent for continued preclinical development as a therapeutic intervention against MRSA.[19]

In the present work, the vicinity of the pyridazine moiety of the urea core was explored using two linkers: a) an amide linker; and b) a urea linker. The two-terminal arms (pyridazinyl moiety and phenyl moiety) were subjected to different terminal modifications and/or by installing a spacer as described below.

Figure 2:
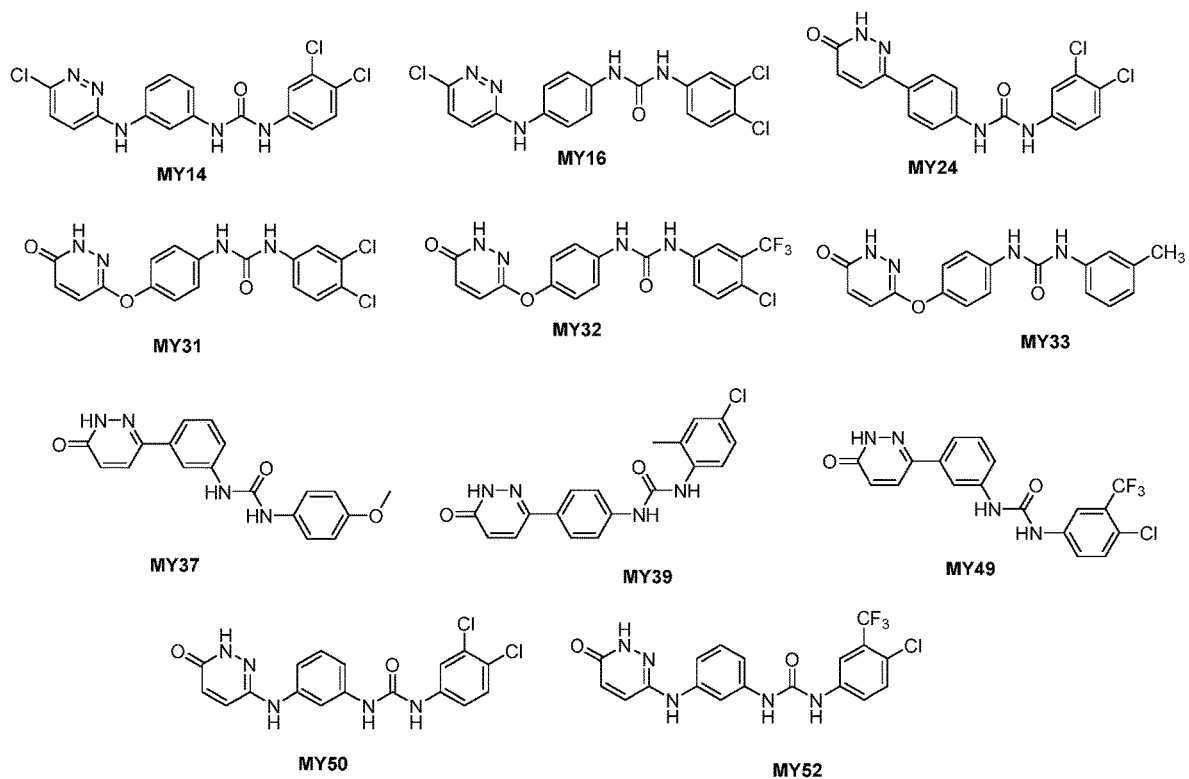
FIG. 2. Medicinal chemistry rational for designing the antimicrobial compounds disclosed herein.

Compounds that were tested are depicted in FIG. 2.
Initial Screening Against Gram Positive Bacteria, Gram Negative Bacteria and *Candida albicans*

The minimum inhibitory concentration (MIC in μg/mL) of MY compounds as well as control drugs (gentamicin, linezolid, vancomycin, Fluconazole and 5-fluorocytosine (5-FC) were initially screened against, methicillin-resistant *Staphylococcus aureus* NRS384 (MRSA USA300); *Escherichia coli* JW55031 (TolC mutant); *Escherichia coli* BW25113 (wild-type); *Clostridium difficile* (ATCC-BAA1870); and *Candida albicans* (ATCC 64124). None of the tested compounds showed activity against wild type *E. coli* or *C. albicans*. Compounds (MY21, MY24 and MY31) exhibited potent activity against MRSA USA300 and *C. difficile* with MIC values ranging from 0.5 to 1 μg/mL. They are as effective as linezolid and vancomycin, the drugs of last resort for treatment of MRSA infections. Moreover, they exhibited potent activity against *C. difficile*; one of the most contagious microorganisms. According to CDC, it is considered as an immediate public health threat that requires urgent action. Compounds (MY14 and MY16) also exhibited potent activity against MRSA USA300 and *C. difficile* (they were less potent than MY21, MY24 and MY31) with MIC values ranging from 1 to 4 μg/mL

TABLE 1

The minimum inhibitory concentration (MIC in μg/mL) of MY compounds and control drugs (gentamicin, linezolid, vancomycin, Fluconazole and 5-fluorocytosine (5-FC) initially screened against, Methicillin-resistant *Staphylococcus aureus* NRS384 (MRSA USA300); *Escherichia coli* JW55031 (TolC mutant); *Escherichia coli* BW25113 (wild-type); *Clostridium difficile* (ATCC-BAA1870); and *C. albicans* (ATCC 64124).

| Compounds/Control Antibiotics | Bacterial Strains | | | | |
| --- | --- | --- | --- | --- | --- |
| | *S. aureus* (MRSA USA300) | *E. coli* (TolC mutant) | *E. coli* (Wild-type) | *C. difficile* (ATCC-BAA1870) | *C. albicans* (ATCC 64124) |
| MY14 | 4 | 2 | >128 | 4 | >128 |
| MY16 | 4 | 16 | >128 | 1 | >128 |
| MY24 | 1 | 1 | >128 | 1 | >128 |
| MY31 | 0.5 | 0.5 | >128 | 1 | >128 |
| MY32 | >128 | >128 | >128 | >128 | >128 |
| MY33 | >128 | >128 | >128 | >128 | >128 |
| MY37 | >128 | 64 | >128 | 64 | >128 |
| MY39 | >128 | 32 | >128 | 16 | >128 |
| MY49 | >128 | >128 | >128 | >128 | >128 |
| MY50 | >128 | 128 | >128 | >128 | >128 |
| MY52 | >128 | >128 | >128 | >128 | >128 |
| Sorafenib | 4 | 1 | >128 | 1 | >128 |
| Linezolid | 1 | 8 | >64 | NT[1] | NT |
| Vancomycin | 1 | NT | NT | 1 | NT |
| Gentamicin | NT | 0.25 | 0.5 | NT | NT |
| 5-Fluorocytosine | NT | NT | NT | NT | 0.25 |
| Fluconazole | NT | NT | NT | NT | >128 |

[1]NT = Not tested

Screening of Active MY Compounds Against Antibiotic-Resistant Gram Positive Bacteria Based upon the initial results obtained, the active compounds were further screened against additional clinical isolates of methicillin-sensitive *S. aureus* (MSSA), methicillin-resistant *S. aureus* (MRSA), vancomycin-resistant *S. aureus* (VRSA), *Staphylococcus epidermidis*, vancomycin-resistant *Enterococcus faecium* (VRE), vancomycin-resistant *Enterococcus faecalis* (VRE) and *Streptococcus pneumoniae*, as presented in Table 2. Additionally, we examined whether the compounds were bacteriostatic (inhibit bacteria from growing) or bactericidal (kill bacteria) by determining the minimum bactericidal concentration (MBC). The MBC was determined by plating 5 μL from each well where no growth was present (in the MIC plates) onto tryptic soya agar plates and incubating plates at 37° C. for 24 hours. The MBC was categorized as the lowest concentration that generated a 99.9% reduction in bacterial colony-forming units (Table 3).

TABLE 2

The minimum inhibitory concentration (MIC in μg/mL) of the active MY compounds against Methicillin-sensitive *Staphylococcus aureus* ATCC-6538 (MSSA ATCC-6538); Methicillin-sensitive *Staphylococcus aureus* (MSSA NRS-107); Methicillin-resistant *Staphylococcus aureus* (MRSA NRS-119); Methicillin-resistant *Staphylococcus aureus* (MRSA NRS-123, USA400); Vancomycin-resistant *Staphylococcus aureus* (VRSA10); Vancomycin-resistant *Staphylococcus aureus* (VRSA12); *Staphylococcus epidermidis* (NRS-101); Cephalosporin-resistant *Streptococcus pneumoniae* ATCC-15916 (*S. pneumonia* ATCC-15916); Cephalosporin-resistant *Streptococcus pneumoniae* ATCC-700677 (*S. pneumonia* ATCC-700677); Vancomycin-resistant *Enterococcus fecalis* ATCC-51299 (VRE ATCC-51299); Vancomycin-resistant *Enterococcus faecium* ATCC-700221 (VRE ATCC-700221); and *Listeria monocytogenes* ATCC-19111 (*L. monocytogenes* ATCC-19111).

| Bacterial Strain | MY14 | MY16 | MY21 | MY24 | MY31 | sorafenib | Linezolid | Vancomycin |
|---|---|---|---|---|---|---|---|---|
| MSSA ATCC-6538 | 2 | 1 | 1 | 1 | 0.5 | 4 | 0.5 | 1 |
| MSSA NRS-107 | 4 | 1 | 1 | 1 | 0.5 | 8 | 1 | 2 |
| MRSA NRS119 | 4 | 1 | 1 | 1 | 0.5 | 2 | 64 | 1 |
| MRSA NRS123 (USA400) | 4 | 1 | 1 | 1 | 0.5 | 4 | 1 | 1 |
| VRSA10 | 2 | 1 | 1 | 1 | 0.5 | 4 | 1 | 64 |
| VRSA12 | 4 | 2 | 1 | 2 | 1 | 2 | 1 | 64 |
| *S. epidermidis* NRS 101 | 8 | 0.5 | 1 | 1 | 0.5 | 8 | 0.5 | 2 |
| *S. pneumoniae* ATCC-15916 | 4 | 2 | 2 | 2 | 0.5 | 4 | 1 | 1 |
| *S. pneumoniae* ATCC 700677 | 4 | 2 | 2 | 2 | 0.5 | 4 | 1 | 1 |
| VRE ATCC-51299 | 64 | 4 | 4 | 4 | 2 | >64 | 1 | 32 |
| VRE ATCC-700221 | 32 | 2 | 2 | 4 | 1 | >64 | 1 | >64 |
| *L. monocytogenes* ATCC-19111 | 8 | 1 | 0.5 | 1 | 0.5 | 4 | 0.5 | 1 |

TABLE 3

The minimum bactricidal concentration (MBC in μg/mL) of the active MY compounds against Methicillin-sensitive *Staphylococcus aureus* ATCC-6538 (MSSA ATCC-6538); Methicillin-sensitive *Staphylococcus aureus* (MSSA NRS-107); Methicillin-resistant *Staphylococcus aureus* (MRSA NRS-119); Methicillin-resistant *Staphylococcus aureus* (MRSA NRS-123, USA400); Vancomycin-resistant *Staphylococcus aureus* (VRSA10); Vancomycin-resistant *Staphylococcus aureus* (VRSA12); *Staphylococcus epidermidis* (NRS-101); Cephalosporin-resistant *Streptococcus pneumoniae* ATCC-15916 (*S. pneumonia* ATCC-15916); Cephalosporin-resistant *Streptococcus pneumoniae* ATCC-700677 (*S. pneumonia* ATCC-700677); Vancomycin-resistant *Enterococcus fecalis* ATCC-51299 (VRE ATCC-51299); Vancomycin-resistant *Enterococcus faecium* ATCC-700221 (VRE ATCC-700221); and *Listeria monocytogenes* ATCC-19111 (*L. monocytogenes* ATCC-19111).

| Bacterial Strain | MY14 MBC | MY16 MBC | MY21 MBC | MY24 MBC | MY31 MBC | sorafenib MBC | Linezolid MBC | Vancomycin MBC |
|---|---|---|---|---|---|---|---|---|
| MSSA ATCC-6538 | 32 | 32 | 4 | >64 | >64 | >64 | 8 | 2 |
| MSSA NRS-107 | 8 | 2 | 4 | 16 | 2 | >64 | 16 | 2 |
| MRSA NRS119 | 8 | 1 | 1 | 32 | 2 | >64 | >64 | 1 |
| MRSA NRS123 (USA400) | 8 | 4 | 8 | >64 | >64 | >64 | 64 | 2 |
| VRSA10 | 8 | 16 | 2 | >64 | >64 | >64 | >64 | >64 |
| VRSA12 | 32 | 8 | 8 | >64 | >64 | >64 | 16 | >64 |

TABLE 3-continued

The minimum bactricidal concentration (MBC in μg/mL) of the active MY compounds against Methicillin-sensitive *Staphylococcus aureus* ATCC-6538 (MSSA ATCC-6538); Methicillin-sensitive *Staphylococcus aureus* (MSSA NRS-107); Methicillin-resistant *Staphylococcus aureus* (MRSA NRS-119); Methicillin-resistant *Staphylococcus aureus* (MRSA NRS-123, USA400); Vancomycin-resistant *Staphylococcus aureus* (VRSA10); Vancomycin-resistant *Staphylococcus aureus* (VRSA12); *Staphylococcus epidermidis* (NRS-101); Cephalosporin-resistant *Streptococcus pneumoniae* ATCC-15916 (*S. pneumonia* ATCC-15916); Cephalosporin-resistant *Streptococcus pneumoniae* ATCC-700677 (*S. pneumonia* ATCC-700677); Vancomycin-resistant *Enterococcus fecalis* ATCC-51299 (VRE ATCC-51299); Vancomycin-resistant *Enterococcus faecium* ATCC-700221 (VRE ATCC-700221); and *Listeria monocytogenes* ATCC-19111 (*L. monocytogenes* ATCC-19111).

| Bacterial Strain | MY14 MBC | MY16 MBC | MY21 MBC | MY24 MBC | MY31 MBC | sorafenib MBC | Linezolid MBC | Vancomycin MBC |
|---|---|---|---|---|---|---|---|---|
| *S. epidermidis* NRS 101 | 64 | 1 | 4 | 8 | 1 | >64 | 8 | 2 |
| *S. pneumoniae* ATCC-15916 | 64 | 4 | 4 | 64 | 4 | >64 | 32 | 1 |
| *S. pneumoniae* ATCC 700677 | >64 | 4 | 4 | >64 | 2 | >64 | 16 | 2 |
| VRE ATCC-51299 | >64 | >64 | 16 | >64 | >64 | >64 | 16 | 64 |
| VRE ATCC-700221 | >64 | 8 | 4 | 16 | 4 | >64 | 16 | >64 |
| *L. monocytogenes* ATCC-19111 | >64 | 32 | 0.5 | 64 | >64 | >64 | 32 | 2 |

The results revealed that most of the MY compounds produced their antibacterial activity via a bacteriostatic mechanism. In agreement with the previous results against MRSA USA300, compounds (MY16, MY21, MY24 and MY31) exhibited potent activity against the tested panel of multi-drug resistant staphylococcal strains with MIC values ranging from 0.5 to 1 μg/mL. Compound (MY21) appeared to be bactericidal (kill the bacteria) as its MBC values were less than three-fold higher than their corresponding MIC values. Compounds (MY24 and MY31) might be bacteriostatic as their MBC values were three-fold (or more) higher than their corresponding MIC values. Interestingly, they retained their antimicrobial activity against the clinically relevant resistant Gram-positive bacteria (Streptococci, Enterococci and *Listeria*) with MIC values ranging from 0.5 to 4 μg/mL.

Figure 3:
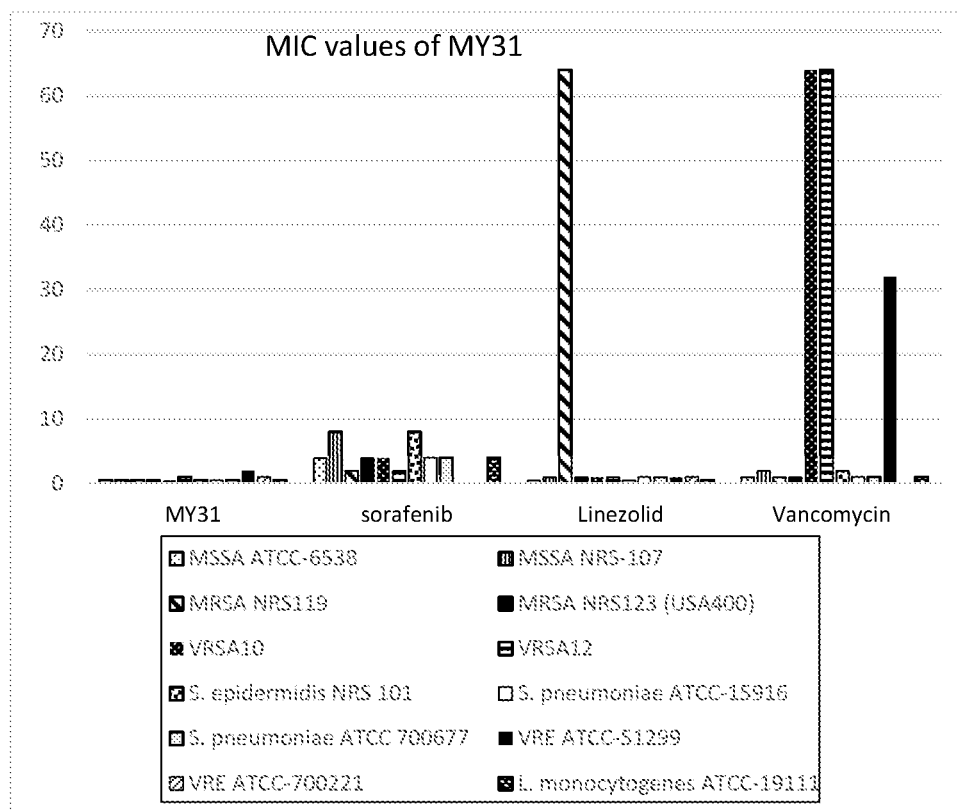
FIG. 3. Relative MIC of MY31 compared to reference drugs.

Furthermore, the compound (MY14) exhibited good activity against the tested staphylococcal strains, inhibiting them at concentrations ranging from 2 to 8 μg/mL. Furthermore, the compounds exhibited moderate activity against *Streptococcus pneumonia* and *Listeria monocytogenes* with MIC values ranging from 4 to 8 μg/mL. Also, they showed poor activity against the vancomycin-resistant Enterococci (VRE) which is typical for many drugs targeting Gram-positive bacteria that they have a little activity against VRE. MY31 demonstrated the highest bacteriostatic activity among the tested compounds, including the positive control antibiotics (FIG. 3). For instance, it stopped the growth of VRSA strains with more potency than sorafenib (the prototype) and, as expected, much higher than vancomycin. In fact, MY31 showed much higher activities than sorafenib in all assays. It also showed much higher potency against one MRSA strain (MRSA NSR119) than linezolid. When compared to linezolid, it demonstrated either equal or higher potency against most of the Gram-positive strains.

Material and Methods

Synthesis of "MY" Compounds

In our theme towards examination the correlation between anti-angiogenesis and anti-MRSA, urea derivatives containing pyridazine moiety, which were published in previous work (Jaballah, et al. Towards Discovery of Novel Scaffold with Potent Antiangiogenic Activity; Design, Synthesis of Pyridazine Based Compounds, Impact of Hinge Interaction, and Accessibility of Their Bioactive Conformation on VEGFR-2 Activities. *J. Enzyme Inhib. Med. Chem.* 2019, 34 (1), 1573-1589) were incorporated in this study, Table 1. The urea derivatives 8(a-m) were obtained via the reaction between designed amines and aryl isocyanate derivatives as depicted in Scheme 1.

Scheme 1. Reagents and conditions

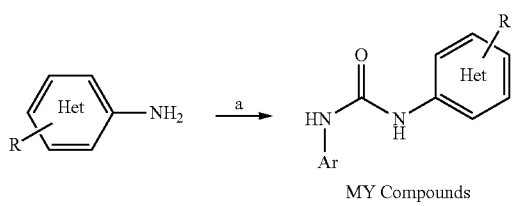

MY Compounds (a) substituted phenylisocyanates, methylene chloride, TEA, r.t.

Experimental

Melting points were measured with a Stuart melting point apparatus and were uncorrected. Infrared spectra were recorded as potassium bromide discs on Schimadzu FT-IR 8400S spectrophotometer and expressed in wave number ($cm^{-1}$). The NMR spectra were recorded by Varian Gemini- 300BB at 300 MHz (Varian Inc., Palo Alto, Calif.) or Bruker spectrophotometer at 400 MHz. 1H NMR spectra were run at 300 or 400 MHz, while 13 C NMR spectra were run at 75 or 100 MHz in deuterated dimethyl sulfoxide (DMSO-d6) or deuterated chloroform (CDCl$_3$). Chemical shifts (dH) are reported relative to TMS as internal standard. All coupling constant (J) values are given in hertz. Chemical shifts (dC) are reported relative to DMSO-d6 as internal standard. The abbreviations used are as follows: s, singlet; d, doublet; m, multiplet. Mass spectra were measured on a GCMSQP1000 EX and Helwett Packard 5988 spectrometers at 70 eV. Elemental analyses were carried out at the Regional Center for Microbiology and Biotechnology, Al-Azhar University, Cairo, Egypt.

Analytical thin layer chromatography on silica gel plates containing UV indicator was employed routinely to follow the course of reactions and to check the purity of products. All reagents and solvents were purified and dried by standard techniques.

Biology

Initial Screening of the Compounds Against Methicillin-Resistant *Staphylococcus aureus*, *Escherichia coli*, *Clostridium difficile* and *Candida albicans* Strains The minimum inhibitory concentrations (MICs) of the tested compounds and control drugs (linezolid, vancomycin, gentamicin (antibiotics) and fluconazole and 5-fluorocytosine (5-FC) (antifungal drugs)) were determined using the broth microdilution method, according to guidelines outlined by the Clinical and Laboratory Standards Institute (CLSI, Clinical and Laboratory Standards Institute, Methods for antimicrobial susceptibility testing of anaerobic bacteria; approved standard, M11-A8. 8$^{th}$ ed., 2012; CLSI, Clinical and Laboratory Standards Institute. M27-A3 Reference Method for Broth Dilution Antifungal Susceptibility Testing of Yeasts; Approved Standard—Third Edition, Wayne, Pa., 2008) against clinically-relevant bacterial (methicillin-resistant *Staphylococcus aureus* (MRSA), *Escherichia coli*, and *C. difficile* strains) and fungal (*Candida albicans*) strains. *S. aureus* and *E. coli* were grown aerobically overnight on tryptone soy agar plates at 37° C. *C. difficile* was grown anaerobically on brain heart infusion supplemented agar at 37° C. for 48 hours. *C. albicans* was grown aerobically overnight on yeast peptone dextrose (YPD) agar plate at 35° C. Afterwards, a bacterial solution equivalent to 0.5 McFarland standard was prepared and diluted in cation-adjusted Mueller-Hinton broth (CAMHB) (for *S. aureus* and *E. coli*) to achieve a bacterial concentration of about 5×10$^5$ CFU/mL. *C. difficile* was diluted in brain heart infusion supplemented broth, supplemented with yeast extract, hemin and vitamin K to achieve a bacterial concentration of about 5×10$^5$ CFU/mL. *C. albicans* was diluted in Roswell Park Memorial Institute (RPMI 1640) medium with glutamine and without bicarbonate (GIBCO by Life Technologies, Green Island, N.Y., USA) which was buffered to pH 7.0 with 0.165 M of [3-(N-morpholino) propanesulfonic acid] (MOPS) (DOT Scientific Inc., Burton, Mich., USA) to achieve a fungal concentration of about 1.5×10$^3$ CFU/mL. Compounds and control drugs were added in the first row of the 96-well plates and serially diluted with the corresponding media containing bacteria. Plates were then incubated aerobically at 37° C. for 18-20 hours (for *S. aureus* and *E. coli*). *C. difficile* was incubated anaerobically at 37° C. for 48 hours. *C. albicans* was incubated aerobically at 37° C. for 24 hours. MICs reported in Table (1) are the minimum concentration of the compounds and control drugs that could completely inhibit the visual growth of bacteria/fungi.

Methods of Screening Against Gram-Positive Bacteria and *C. albicans*

The minimum inhibitory concentrations (MICs) of the tested compounds and control drugs; linezolid, vancomycin, gentamicin (antibiotics) and fluconazole and 5-fluorocytosine (5-FC) (antifungal drugs) were determined using the broth microdilution method, according to guidelines outlined by the Clinical and Laboratory Standards Institute (CLSI)[1, 2, 3] against clinically-relevant bacterial (methicillin-resistant *Staphylococcus aureus* (MRSA), *Escherichia coli* and *Clostridium difficile* strains) and fungal (*Candida albicans*) strain. *S. aureus* and *E. coli* were grown aerobically overnight on tryptone soy agar plates at 37° C. *C. difficile* was grown anaerobically on brain heart infusion supplemented agar at 37° C. for 48 hours. *C. albicans* was grown aerobically overnight on yeast peptone dextrose (YPD) agar plate at 35° C. Afterwards, a bacterial solution equivalent to 0.5 McFarland standard was prepared and diluted in cation-adjusted Mueller-Hinton broth (CAMHB) (for *S. aureus* and *E. coli*) to achieve a bacterial concentration of about 5×10$^5$ CFU/mL. *C. difficile* was diluted in brain heart infusion supplemented broth, supplemented with yeast extract, hemin and vitamin K to achieve a bacterial concentration of about 5×10$^5$ CFU/mL. *C. albicans* was diluted in Roswell Park Memorial Institute (RPMI 1640) medium with glutamine and without bicarbonate (GIBCO by Life Technologies, Green Island, N.Y., USA) which was buffered to pH 7.0 with 0.165 M of [3-(N-morpholino) propanesulfonic acid] (MOPS) (dot scientific inc., Burton, Mich., USA) to achieve a fungal concentration of about 1.5×10$^3$ CFU/mL. Compounds and control drugs were added in the first row of the 96-well plates and serially diluted with the corresponding media containing bacteria/fungi. Plates were then, incubated aerobically at 37° C. for 18-20 hours (for *S. aureus* and *E. coli*). *C. difficile* was incubated anaerobically at 37° C. for 48 hours. *C. albicans* was incubated aerobically at 37° C. for 24 hours. MICs reported in Table (1) are the minimum concentration of the compounds and control drugs that could completely inhibit the visual growth of bacteria/fungi.

REFERENCES (1) Le et al. Repurposing Human Kinase Inhibitors to Create an Antibiotic Active against Drug-Resistant *Staphylococcus aureus*, Persisters and Biofilms. Nat. Chem. 2020, 12 (2), 145-158.

(2) Shalaby et al. Penicillin Binding Protein 2a: An Overview and a Medicinal Chemistry Perspective. Eur. J. Med. Chem. 2020, 112312.

(3) Dokla et al. Development of Benzimidazole-Based Derivatives as Antimicrobial Agents and Their Synergistic Effect with Colistin against Gram-Negative Bacteria. Eur. J. Med. Chem. 2020, 186, 111850.

(4) Harms et al. Mechanisms of Bacterial Persistence during Stress and Antibiotic Exposure. Science (80. 2016, 354 (6318).

(5) US CDC. Antibiotic Resistance Threats in the United States. Centers Dis. Control Prev. 2019, 1-150.

(6) Mancy et al. Balancing Physicochemical Properties of Phenylthiazole Compounds with Antibacterial Potency by Modifying the Lipophilic Side Chain. ACS Infect. Dis. 2020, 6 (1), 80-90.

(7) Tacconelli et al. Discovery, Research, and Development of New Antibiotics: The WHO Priority List of Antibiotic-Resistant Bacteria and Tuberculosis. Lancet Infect. Dis. 2018, 18 (3), 318-327.

(8) Lu et al. Novel Benzyl Phenyl Sulfide Derivatives as Antibacterial Agents against Methicillin-Resistant *Staphylococcus aureus*. J. Antibiot. (Tokyo). 2020, 73 (2), 82-90.
(9) Okumu et al. J. Novel Bacterial Topoisomerase Inhibitors Derived from Isomannide Eur. J. Med. Chem. 2020, 112324.
(10) Pujol et al. Pentafluorosulfanyl-Containing Triclocarban Analogs with Potent Antimicrobial Activity. Molecules 2018, 23 (11), 1-17.
(11) Wall et al. Dimeric Stilbene Antibiotics Target the Bacterial Dimeric Stilbene Antibiotics Target the Bacterial Cell Wall in Drug-Resistant Gram-Positive Pathogens. 2020.
(12) Kurosu et al. Bacterial Protein Kinase Inhibitors. Drug Dev. Res. 2010, 71 (3), 168-187.
(13) Chem. Biodiversity. https://doi.org/10.1002/cbdv.202000100.
(14) Baumann et al. An Overview of the Synthetic Routes to the Best Selling Drugs Containing 6-Membered Heterocycles. 2013, 2265-2319.
(15) Shiroza et al. The Structures of Cirratiomycin A and B, the New Peptide Antibiotics. 2014, 1369.
(16) No, X.; Journal, T. H. E.; Antibiotics, 0. F. FIG. 1. Structure. XXXIV (12).
(17) Dokla et al. Development of Benzimidazole-Based Derivatives as Antimicrobial Agents and Their Synergistic Effect with Colistin against Gram-Negative Bacteria. Eur. J. Med. Chem. 2020, No. March, 111850.
(18) Kini et al. Potentials of Diphenyl Ether Scaffold as a Therapeutic Agent: A Review. Mini-Reviews Med. Chem. 2019, 19 (17), 1392-1406.
(19) Chang et al. In Vitro and in Vivo Activity of a Novel Sorafenib Derivative SC5005 against MRSA. 2015, 1-11.
(20) Jaballah et al. Towards Discovery of Novel Scaffold with Potent Antiangiogenic Activity; Design, Synthesis of Pyridazine Based Compounds, Impact of Hinge Interaction, and Accessibility of Their Bioactive Conformation on VEGFR-2 Activities. J. Enzyme Inhib. Med. Chem. 2019, 34 (1), 1573-1589.

REFERENCES FOR ANTIMICROBIAL TESTING

CLSI, Clinical and Laboratory Standards Institute, Methods for antimicrobial susceptibility testing of anaerobic bacteria; approved standard, M11-A8. 8th ed., 2012.
CLSI, Clinical and Laboratory Standards Institute. M27-A3 Reference Method for Broth Dilution Antifungal Susceptibility Testing of Yeasts; Approved Standard—Third Edition, Wayne, Pa., 2008.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

ACKNOWLEDGEMENT OF SPONSORED RESEARCH

This project was funded by Knowledge Economy and Technology Transfer Center, King Abdulaziz University, Kingdom of Saudi Arabia; Award Number 2020-47.

We claim:
1. A method of treating a methicillin-resistant *Staphylococcus aureus* (MRSA) infection in a subject in need thereof, comprising
administering to the subject a therapeutically effective amount of at east one compound of general Formula I

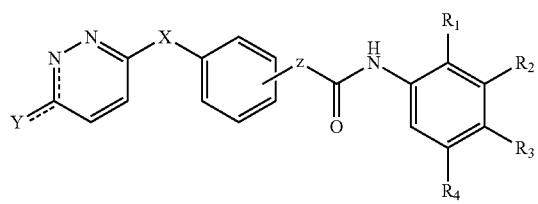

Formula I where:
Y=oxygen, Cl or methoxy;
X=present or absent and if present is oxygen or NH;
Z=3-amino (3-NH) or 4-amino (4-NH) and the attachment between Z and phenyl is ortho, meta or para;
R1 is H, methoxy or methyl;
R2 is H, methyl, chloro, trifluoromethyl or methoxy;
R3 is chloro, methyl or trifluoromethyl;
R4 is H, methyl, methoxy, trifluoromethyl, chloro, fluoro or bromo;
or a free base or pharmaceutically acceptable salt thereof, wherein the at least one compound is:

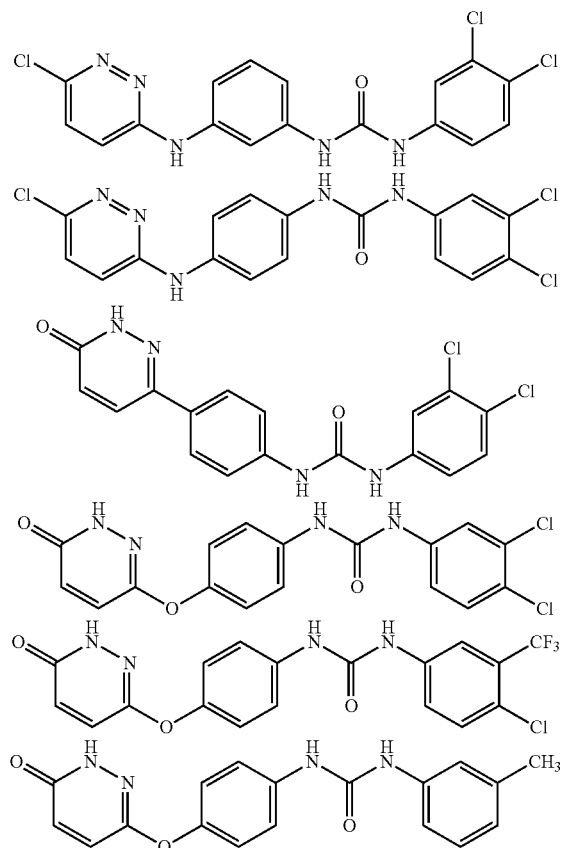

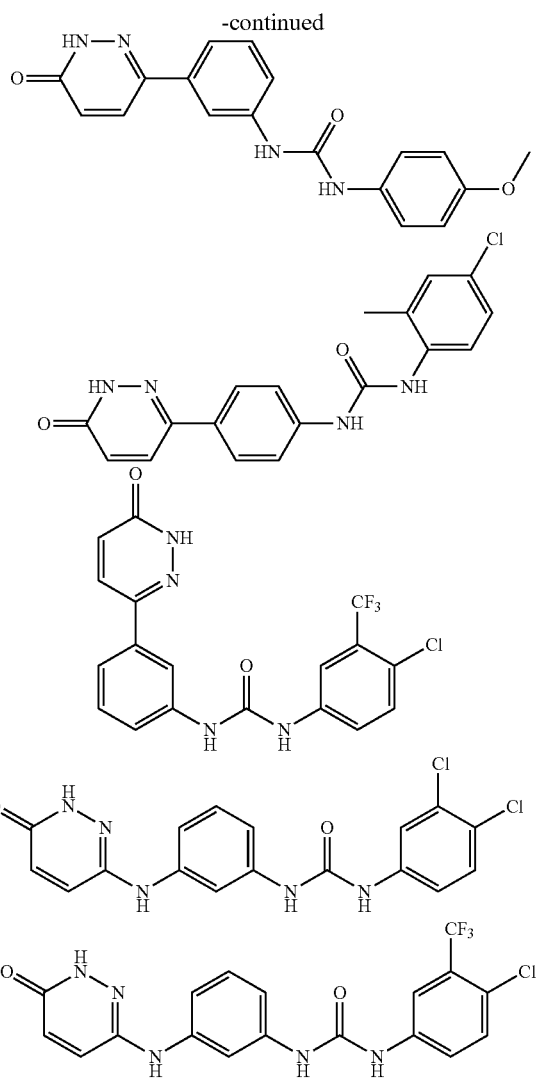

2. The method of claim 1, wherein the at least one compound is:

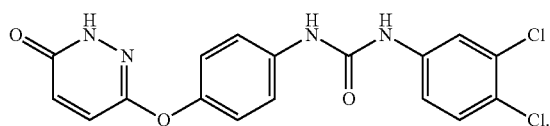 [SMILES: O=C(Nc1ccc(Oc2ccc(=O)[nH]n2)cc1)Nc1ccc(Cl)c(Cl)c1]

3. A method of inhibiting the growth of and/or killing the growth of methicillin-resistant *Staphylococcus aureus*, comprising
contacting the bacterium with a pyridazine compound of general Formula I

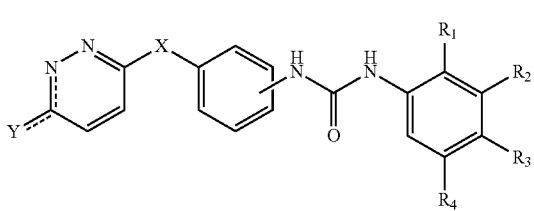

Formula I where:
Y=oxygen, Cl or methoxy, sulfur;
X=present or absent and if present is oxygen or NH;
R1 is H, methoxy or methyl;
R2 is H, methyl, chloro, trifluoromethyl or methoxy;
R3 is chloro, methyl or trifluoromethyl;
R4 is H, methyl, methoxy, trifluoromethyl, chloro, fluoro or bromo; and
the attachment between the urea moiety and the unsubstituted phenyl is ortho, meta or para;
or a free base or pharmaceutically acceptable salt thereof, wherein the pyridazine compound is:

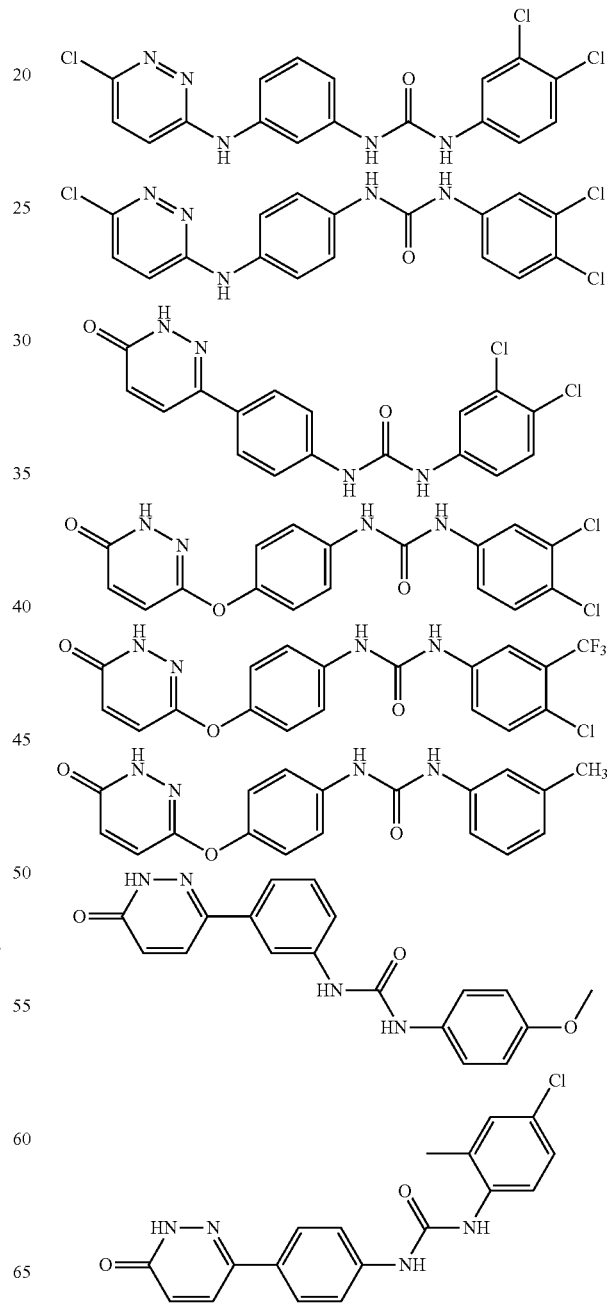

-continued

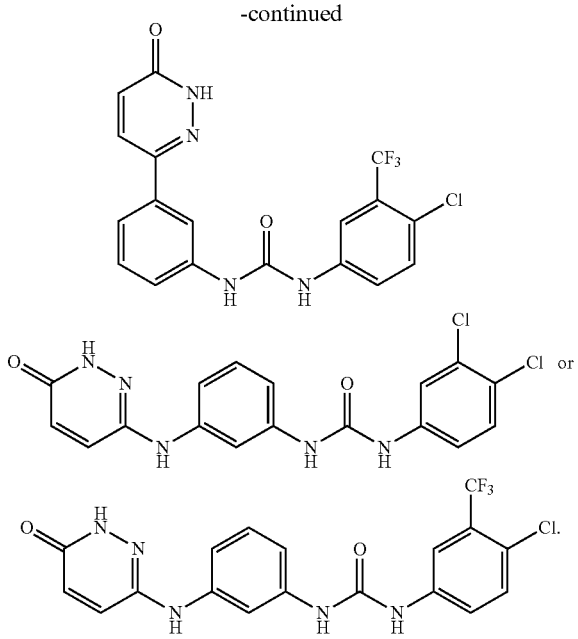

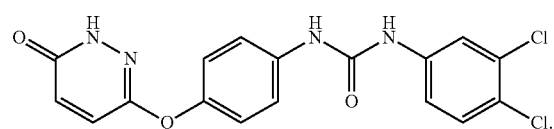 [SMILES: O=C(Nc1ccc(Oc2ccc(=O)[nH]n2)cc1)Nc1ccc(Cl)c(Cl)c1]

4. The method of claim 3, wherein the pyridazine compound is:

5. The method of claim 3, wherein the pyridazine compound is a pharmaceutically acceptable salt.

6. The method of claim 5, wherein the pharmaceutically acceptable salt is an organic salt or an inorganic salt.

7. The method of claim 6, wherein the organic salt is a, mesylate, tosylate, citrate, acetate, maleate, fumarate, lactate, sulfate salt and the inorganic salt is a hydrochloride or hydrobromide salt.

* * * * *